(12) United States Patent
Cattaneo et al.

(10) Patent No.: US 9,855,157 B2
(45) Date of Patent: Jan. 2, 2018

(54) MEDICAL DEVICE FOR INSERTING INTO A HOLLOW ORGAN OF THE BODY

(71) Applicant: ACANDIS GMBH & CO. KG, Pfinztal (DE)

(72) Inventors: Giorgio Cattaneo, Karlsruhe (DE); David Klopp, Remchingen (DE); Frank Nagl, Karlsruhe (DE)

(73) Assignee: ACANDIS GMBH & CO. KG, Pfinztal (DE)

( * ) Notice: Subject to any disclaimer, the term of this patent is extended or adjusted under 35 U.S.C. 154(b) by 6 days.

(21) Appl. No.: 14/888,880

(22) PCT Filed: Apr. 30, 2014

(86) PCT No.: PCT/EP2014/058862
§ 371 (c)(1),
(2) Date: Feb. 9, 2016

(87) PCT Pub. No.: WO2014/177634
PCT Pub. Date: Nov. 6, 2014

(65) Prior Publication Data
US 2016/0158039 A1 Jun. 9, 2016

(30) Foreign Application Priority Data
May 3, 2013 (DE) .................... 10 2013 104 550

(51) Int. Cl.
*A61F 2/915* (2013.01)
*A61F 2/91* (2013.01)
(Continued)

(52) U.S. Cl.
CPC .............. *A61F 2/91* (2013.01); *A61B 17/221* (2013.01); *A61F 2/013* (2013.01); *A61F 2/915* (2013.01);
(Continued)

(58) Field of Classification Search
CPC . A61F 2/82–2/945; A61F 2/24–2/2475; A61F 2250/0006
See application file for complete search history.

(56) References Cited

U.S. PATENT DOCUMENTS

| 6,200,337 B1 | 3/2001 | Moriuchi |
| 7,442,203 B2 | 10/2008 | Ehr |

(Continued)

FOREIGN PATENT DOCUMENTS

| EP | 1448118 B1 | 8/2010 |
| WO | WO 98/44871 A1 | 10/1998 |
| WO | WO 201201163 A1 | 8/2012 |

OTHER PUBLICATIONS

International Search Report and Written Opinion for Corresponding Application PCT/EP2014/058862, published Aug. 6, 2014, partial translation provided.

(Continued)

*Primary Examiner* — Yashita Sharma
*Assistant Examiner* — Rebecca Preston
(74) *Attorney, Agent, or Firm* — Hassan Abbas Shakir; Katten Muchin Rosenman LLP

(57) ABSTRACT

The invention relates to a medical device for inserting into a hollow organ of the body. The device has a compressible and expandable lattice structure made of webs, which are integrally connected to each other by web connectors and which bound closed cells of the lattice structure, wherein the web connectors each have a connector axis extending between two cells which, in a longitudinal direction of the lattice structure, are adjacent to each other. During the transition of the lattice structure from the production state to a compressed state, the web connectors rotate in such a way that an angle between the connector axis and a longitudinal axis of the lattice structure changes, in particular increases, (Continued)

during the transition of the lattice structure from a completely expanded production state to a partially expanded intermediate state.

22 Claims, 7 Drawing Sheets

(51) Int. Cl.
  *A61B 17/221* (2006.01)
  *A61F 2/01* (2006.01)
(52) U.S. Cl.
  CPC .............. *A61F 2002/016* (2013.01); *A61F 2002/91575* (2013.01); *A61F 2210/0014* (2013.01); *A61F 2230/0004* (2013.01); *A61F 2250/0006* (2013.01)

(56) References Cited

U.S. PATENT DOCUMENTS

| 2004/0133271 | A1 | 7/2004 | Jang |
| 2005/0085897 | A1 | 4/2005 | Bonsignore |
| 2006/0142842 | A1* | 6/2006 | Molaei ............ A61F 2/07 623/1.15 |
| 2008/0228261 | A1* | 9/2008 | Anukhin ............ A61F 2/915 623/1.16 |
| 2009/0171426 | A1 | 7/2009 | Magnuson |
| 2010/0211161 | A1 | 8/2010 | Dreher |
| 2011/0202122 | A1 | 8/2011 | Takeuchi |

OTHER PUBLICATIONS

Office Action for Corresponding Application DE 10 2013 104.550.2 dated Dec. 16, 2013, partial translation provided.
International Search Report and Written Opinion for Corresponding Application PCT/EP2014/058862, published Aug. 6, 2014, partial translation provided, (resubmitted for clarity).
Office Action for Corresponding Application DE 10 2013 104.550.2 dated Dec. 16, 2013, partial translation provided, (resubmitted for clarity).
International Search Report for Corresponding Application PCT/EP2014/058862 in English, dated Nov. 12, 2015.
Written Opinion for Corresponding Application PCT/EP2014/058862 in English, dated Nov. 12, 2015.
File history of U.S. Appl. No. 13/818,664.
File history of U.S. Appl. No. 15/351,746.

* cited by examiner

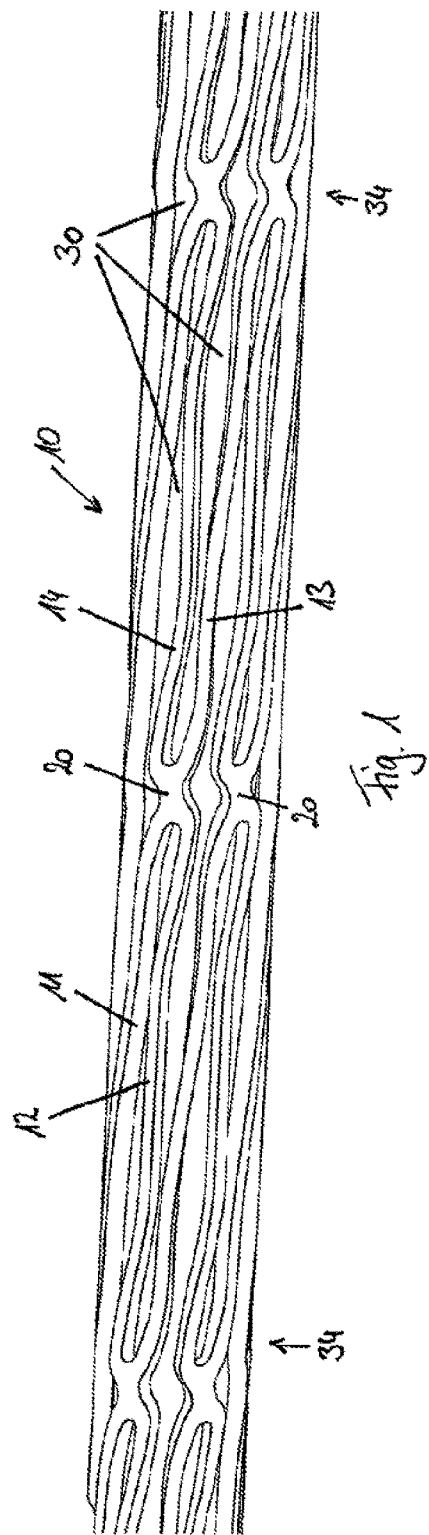
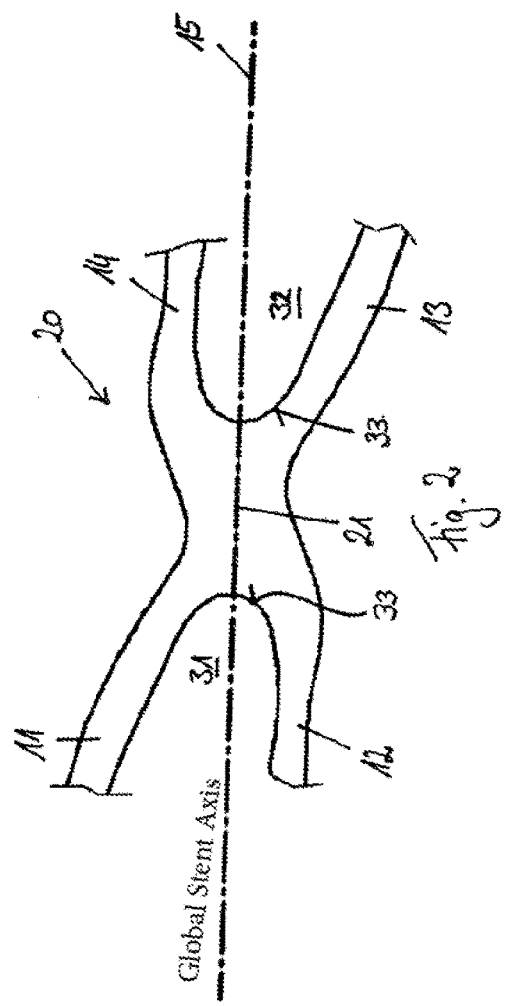

MEDICAL DEVICE FOR INSERTING INTO A HOLLOW ORGAN OF THE BODY

BACKGROUND OF THE INVENTION

1. Field of the Invention

The invention relates to a medical device for insertion into a hollow organ of the body.

2. Background of the Invention

Devices of this type are known, for example, as stents or thrombectomy devices. Stents or thrombectomy devices are used to treat a variety of diseases of the blood vascular system and frequently have an expandable lattice structure. The lattice structure is guided to the treatment site via a catheter. To this effect, the lattice structure assumes a radially compressed state so that it can be pushed along within the catheter canal.

In order to ensure good guidability, it is useful for the lattice structure to have a relatively high axial stiffness, at least in the guiding state. This prevents the lattice structure from radially widening when subjected to an axial force, causing increased friction at the interior wall of the catheter. In the known stents or thrombectomy devices, an increased axial stiffness leads to a reduction of cross-axial flexibility, making it more difficult to place the lattice structure in small, tightly wound blood vessels, such as are found in the area of the cerebral vascular system, for example.

As a rule, when designing medical devices with an expandable lattice structure, as is the case with stents and thrombectomy devices, it is necessary to find a compromise between high cross-axial flexibility and a sufficient radial force. The radial force serves to expand the lattice structure radially and to support it against a vascular wall. By changing the dimensions, such as those of the web cross sections, the cross-axial flexibility can be increased, so that the device or lattice structure can be easily guided through small, highly wound blood vessels. At the same time, however, the radial expandability or radial force is diminished. Consequently, there is a risk that the radial force will no longer be sufficient to securely anchor the lattice structure within the blood vessel.

SUMMARY OF THE INVENTION

It is an object of the present invention to provide a medical device for insertion into a hollow organ of the body, having sufficient radial force for anchorage inside the organ, good axial stiffness to guide it through a catheter, and high cross-axial flexibility so that the device is easy to guide through small, hollow, highly wound vessels of the body.

The invention is thus based on the idea of providing a medical device for insertion into a hollow organ of the body, having a compressible and expandable lattice structure of webs that are integrally connected to each other by web connectors that delimit closed cells of the lattice structure. Each web connector has a connector axis that extends between two cells that, in a longitudinal direction of the lattice structure, are adjacent to each other. During the transition of the lattice structure from the production state to a compressed state, the web connectors rotate in such a way that an angle between the connector axis and a longitudinal axis of the lattice structure changes, in particular increases, during the transition of the lattice structure from a completely expanded production state to a partially expanded intermediate state.

In principle, the lattice structure of the medical device of this invention can be of one piece. The webs of the lattice structure can be cut from a tubular blank by a laser cutter, for example. The cut-out areas form the cells that are delimited by the webs. The invention preferably entails a lattice structure having a closed cell design. The cells are thus completely enclosed by webs. In particular, the cells can have an essentially rhomboidal basic shape. In other words, each cell is preferably delimited by four webs.

Each web connector that integrally forms a part of the lattice structure can therefore connect four webs with each other. The web connectors essentially form the crossing points of the webs.

Compressing or expanding the lattice structure alters the height and width of the individual cells of the lattice structure. Rotating the web connectors affects the degree of change in the height and width of the cell. In particular, the rotation of the web connectors results in a varying, dynamically changing relationship between cell height and cell width. This results in a comparatively high flexibility of the lattice structure, particularly in a cross-axial direction. In particular, rotating the web connectors allows the lattice structure to take on an oval shape when guided through narrow hollow body organs. The lattice structure, which at least in some sections can have a cylindrical cross section, can thus assume an oval cross-sectional geometry when it is guided through a curved blood vessel. As a result, the medical device can also be inserted in very small hollow body organs or blood vessels with pronounced vascular curvatures.

The angle between the connector axis and the longitudinal axis in the production state and/or in a compressed guiding state of the lattice structure can be a maximum of 5 o, in particular a maximum of 4 degrees, in particular a maximum of 3 degrees, in particular a maximum of, in particular a maximum of 1 degrees. Certain embodiments of the invention allow for the connector axis in the production state and/or in a compressed guiding state of the lattice structure to be aligned parallel to the longitudinal axis of the lattice structure. In particular, in the production state the connector axis can be aligned parallel, and in a partially expanded intermediate state of the lattice structure the connector axis can be aligned at an angle to the longitudinal axis of the lattice structure. Aligning the connector axis in the production state parallel to the longitudinal axis of the lattice structure ensures that the lattice structure has high axial stability, since the cells and webs, arranged longitudinally adjacent to each other, support each other in this manner.

In general, the rotation of the web connectors increases the flexibility of the lattice structure, specifically without impairing stability in the expanded or implanted state. Flexibility is thus increased without diminishing the radial force.

The rotation of the web connector occurs preferably on a plane of the wall of the lattice structure. In general, the lattice structure can be cylindrical in sections, with the cylindrical surface area defining the wall plane. In other words, the web connector can rotate about a rotational axis that is positioned vertically on the longitudinal axis of the lattice structure.

In a preferred embodiment of the medical device of this invention, the connector axis is aligned parallel to the longitudinal axis of the lattice structure in a compressed state, in particular in a guiding state. In particular, [the embodiment] can provide for the connector axis to be aligned parallel to the longitudinal axis of the lattice structure, both in the production state and the compressed state, in particular in the guiding state. Specifically, the web connector can change the rotational direction during the transition of the lattice structure from the production state to the compressed state, in particular the guiding state.

The guiding state corresponds to a compressed state, wherein the lattice structure has a degree of expansion sufficiently small to keep the lattice structure within a guiding system. The degree of expansion can be 10% or less. In this way, the lattice structure can be introduced into small guiding systems, such as catheters, with ease. In general, in intermediate states of the lattice structure, in particular between the guiding state and the production state, [the invention] allows for each web connector to have a connector axis that is aligned at an angle to the longitudinal axis of the lattice structure.

It is generally pointed out that any reference to an angle between the longitudinal axis of the lattice structure and the connector axis of the web connector within the framework of the present application actually relies on a projection of the longitudinal axis of the lattice structure in the wall plane, i.e., the plane of the web connectors. The angle between the connector axis and the longitudinal axis of the lattice structure is thus shown particularly in a lateral view of the medical device or lattice structure.

The connector axis preferably corresponds to the shortest distance between the tips of two cells located longitudinally on opposite sides of the web connector. The lattice structure generally comprises a plurality of cells arranged both longitudinally and circumferentially in relation to the lattice structure. The cells are separated from each other by webs and web connectors. In particular, the web connectors separate cells from each other in the longitudinal direction of the lattice structure. The shortest distance between two cells that are arranged immediately adjacent to each other constitutes the connector axis. The connector axis thus extends along a line through the web connector, the said line extending from a first cell to a longitudinally adjacent second cell. The shortest connecting line between the two cells, by way of the web connector, corresponds to the connector axis.

In a further preferred embodiment of the invention, each of the adjacent cells of the lattice structure that are arranged longitudinally comprises a cell tip with a curvature. The curvature can have a maximum or a vertex that forms an end point of the connector axis. In general, webs that are arranged adjacent to each other in a circumferential direction of the lattice structure can be merged in a web connector at their longitudinal ends. This can create a curvature between adjacent webs arranged in a circumferential direction that simultaneously represents a cell boundary. In particular, the curvature delimits a cell tip, specifically the tip of a closed cell that preferably has a rhomboidal basic form. The corners of the rhomboid essentially form the cell tips. These are not necessarily pointy in the sense of a sharp delimitation, but can be curved. The curvature can generally take the form of a parabola, thereby creating a maximum. Preferably, the maximum or the vertex of the curvature forms the end point of the connector axis.

In a further preferred embodiment of the device of this invention, the connector axis transects, at least in a partially expanded state of the lattice structure, the longitudinal axis of the lattice structure at an intersection that forms a rotational point around which the web connector rotates. The rotational point can simultaneously form a symmetry point.

In particular, [the invention] can provide for the web connector to be point-symmetrical with respect to the rotational point.

In principle, four webs can each be arranged on a web connector, wherein a first and third web and a second and fourth web are arranged on diametrically opposing sides. Specifically, a first web can be arranged diametrically opposite to a third web, and a second web diametrically opposite a fourth web. Each web can have a neutral fiber. The neutral fiber corresponds to a line or area of the longitudinal section of the web, the length of which does not change when the web is deformed. Preferred embodiments allow in each case for a neutral fiber of the second and third web to be positioned vertically upon the neutral fibers of the first and third web. Generally, the neutral fiber of the second web can be aligned vertically to the neutral fiber of the first web. The neutral fiber of the fourth web can be aligned vertically to the neutral fiber of the third web. In principle, other angles are possible as well. The neutral fibers can, for example, enclose an angle between two webs connected within the web connector, said angle measuring a maximum of 90 degrees, in particular a maximum of 75 degrees, in particular a maximum of 55 degrees, in particular a maximum of 50 degrees, in particular a maximum of 45 degrees.

The neutral fibers of the second and the fourth web can be arranged in alignment with each other. In other words, the first and the third web can share a continuous neutral fiber. It is therefore preferred for the neutral fibers of the second and the fourth web to be arranged staggered to each other. In other words, the neutral fibers of the second and fourth web can meet the neutral fibers of the first and third web at a distance from each other. This enhances the rotation of the web connector and thus the flexibility of the lattice structure.

The second and the fourth web can each have a broadened root. The webs usually have a width that is constant over most of the web length. In the area of the web connector, particularly at the transition to the web connector, diametrically opposing webs at least, namely the second and the fourth web can have a broadened root. This increases the stability of the web connector and particularly that of the entire lattice structure.

The second and fourth web can take an S-shaped course in the area of the web connector. The first and third web, particularly the neutral fiber thereof, can essentially take a straight course. In particular, the second and fourth web can have a bend that transitions into an end section of the web, particularly an angular end section, facilitating the transition into the web connector. The bend or the kink forms a deformation zone that contributes to the compression or, respectively, the expansion of the lattice structure.

Overall, an expansion or compression is achieved, which in general means a radial change of the size of the cross section of the lattice structure by means of the deformation of the webs of the lattice structure. The bend or the kink at the web ends at the transition into the web connector, creating defined sites where the webs are deformed, making any deformation of the webs easy to foresee. By means of the first and third webs that are essentially aligned with each other to create an essentially straight web course, the stability of the lattice structure is enhanced.

In a further preferred embodiment, the web connector can have a wasp-waisted shape. The wasp-waisted shape appears, in particular, as a tapering of the cross section of the web connector, wherein the cross section is preferably formed in a circumferential direction of the lattice structure. The wasp-waisted embodiment of the web connector further enhances the flexibility of the lattice structure, particularly without any negative effect on the radial force.

To achieve high bending flexibility and longitudinal-axial stability of the lattice structure in a guiding state, it is preferred if the connector axis, at an expansion degree of the lattice structure of 5% to 15%, in particular 8% to 12%, in particular 10% or 9.9%, at an angle of not more than 5 degrees, in particular not more than 4 degrees, in particular not more than 3 degrees, in particular not more than 2 degrees, in particular not more than 1 degrees, is aligned to the longitudinal axis of the lattice structure. At an expansion degree of the lattice structure of 5% to 15%, in particular 8% to 12%, in particular 10% or 9.9%, the connector axis can also be aligned parallel to the longitudinal axis of the lattice structure.

Alternatively or additionally, at an expansion degree of at least 90%, in particular at least 95%, in particular at least 98%, in particular 100%, at an angle of not more than 5 degrees, in particular not more than 4 degrees, in particular not more than 3 degrees, in particular not more than 2 degrees, in particular not more than 1 degrees, the connector can be aligned to the longitudinal axis of the lattice structure. At an expansion degree of the lattice structure of at least 90%, in particular at least 95%, in particular at least 98%, in particular 100%, the connector axis can also be aligned parallel to the longitudinal axis of the lattice structure. The 100% expansion degree corresponds to the fully expanded production state of the lattice structure.

The following applies to the intermediate states of the lattice structure:

At an expansion degree of 40% to 50%, in particular 42% to 48%, in particular 44.4%, the connector axis with the longitudinal axis of the lattice structure can enclose an angle of 15 degrees to 20 degrees, in particular 16 degrees to 19 degrees, in particular 18 degrees.

Moreover, at an expansion degree of 60% to 70%, in particular 62% to 68%, in particular 66.7%, the connector axis with the longitudinal axis of the lattice structure can enclose an angle of 12 degrees to 18 degrees, in particular 13 degrees to 17.5 degree, in particular 14 degrees to 17 degrees, in particular 16 degrees.

At an expansion degree of 80% to 90%, in particular 82% to 90%, in particular 84% to 89.5%, in particular 86% to 89%, in particular 88.9%, it is also conceivable for the connector axis with the longitudinal axis of the lattice structure to enclose an angle of 5 degrees to 12 degrees, in particular 6 degrees to 11 degrees, in particular 7 degrees to 10 degrees, in particular 8 degrees.

The aforementioned expansion degrees and ranges of expansion degrees can be randomly combined with their correlated angles and angle ranges. Particularly preferred embodiments provide, for example, for the connector axis, at an expansion degree of the lattice structure of 9.9% and/or 100%, to be aligned parallel to the longitudinal axis of the lattice structure. At an expansion degree of 44.4%, the connector axis with the longitudinal axis of the lattice structure can enclose an angle of 18 degrees, at an expansion degree of 66.1% an angle of 16 degrees can be enclosed, and at an expansion degree of 88.9%, an angle of 8 degrees can be enclosed.

The lattice structure can generally be provided as self-expandable. Specifically, the lattice structure can include a super-elastic material, particularly a nickel-titanium alloy, preferably nitinol. The lattice structure can also be made of one piece. In particular, the lattice structure can consist of a super-elastic material, in particular a nickel-titanium alloy, such as nitinol. Super-elastic materials of the aforementioned type have a high elasticity that facilitates the rotation of the web connectors, in particular without plastic deformation. Moreover, super-elastic materials of this type provide sufficient radial force to allow for radial expansion of the lattice structure, even against the resistance of a vascular wall. Nickel-titanium alloys also have shape memory properties that contribute advantageously to self-expandability.

With respect to the dimensions of the lattice structure, it is of advantage when the lattice structure in the production state has a cross sectional diameter of between 3.5 mm and 6 mm, in particular 3.5 mm or 4.5 mm, or 6 mm. The aforementioned values apply to the production state in which the lattice structure is fully expanded. In the implanted state the lattice structure preferably has a cross-sectional diameter that is smaller by 0.5 mm to 1.5 mm than in the production state. This ensures that the lattice structure generates sufficient radial force to be firmly anchored in a vessel of the body.

In addition, in the circumferential direction the lattice structure can have between three and six, in particular between three and nine, preferably six, immediately adjoining cells that form a cell ring. In other words, in preferred embodiments the lattice structure has a ring of cells, wherein the number of cells is limited to the aforementioned values or the ranges of values. Additional embodiments can provide for the lattice structure in the circumferential direction to have more than twelve, in particular between twelve and 48, immediately adjacent cells that form a cell ring.

In general, the lattice structure can have cells, each of which is delimited by four webs. A first and a third web can have a first web width, and a second and fourth web can have a second web width. The ratio between the first web width and the second web width lies preferably between 1:1.1 and 1:3, in particular between 1:1.1 and 1:1.5, in particular between 1:1.25 and 1:1.5, in particular between 1:1.1 and 1:1.3, and is preferably 1:1.3, 1:1.25 or 1:1.2. The web width ratio affects the rotatability of the web connector and ensures sufficient radial expandability of the lattice structure in highly wound vascular anatomies.

To achieve an optimum web width ratio, the number of cells in a cell ring of the lattice structure must also be considered. In a lattice structure that has a cell ring with three to nine cells, in particular six cells, it is therefore preferred when the ratio between the first web width and the second web width is preferably between 1:1.1 and 1:1.5, in particular between 1:1.1 and 1:1.3, and preferably 1:1.3. In a lattice structure having a cell ring with more than twelve cells, in particular between twelve and 48, the ratio between the first web width and the second web width lies preferably between 1:1.1 and 1:3, in particular 1:1.25 or 1:1.2.

BRIEF DESCRIPTION OF THE DRAWINGS

In the following, the invention is explained in greater detail by means of an exemplary embodiment and with reference to the enclosed schematic drawings. The drawings show:

FIG. 1: a lateral view of a medical device according to this invention in a guiding state, in particular at an expansion degree of 9.9%;

FIG. 2. a detail view of a web connector of the medical device according to FIG. 1;

DETAILED DESCRIPTION OF THE INVENTION

The accompanying figures show a medical device suited for insertion into a hollow body organ. To this effect, the medical device has, in particular, a lattice structure 10 that is compressible and expandable. In other words, the lattice structure 10 can assume a guiding state in which the lattice structure 10 has a relatively small cross-sectional diameter. The lattice structure 10 is preferably self-expandable, so that the lattice structure 10 automatically expands to a maximum cross-sectional diameter without the influence of external forces. The state in which the lattice structure 10 has a maximum cross-sectional diameter corresponds to the production state. In the production state the lattice structure 10 has an expansion degree of 100%. An expansion degree of 100% thus corresponds to the maximum cross-sectional diameter which the lattice structure 10 can automatically assume. In this state the lattice structure 10 exerts no radial force of any kind.

The lattice structure 10 is preferably formed of one piece. In particular, the lattice structure 10 can be cylindrical, at least in some sections. The lattice structure 10 is preferably made of a tubular blank by a laser-cutting method. The laser cutting process exposes the individual webs 11, 12, 13, 14 of the lattice structure. The areas removed from the blank form cells 30 of the lattice structure 10.

Figure 9:
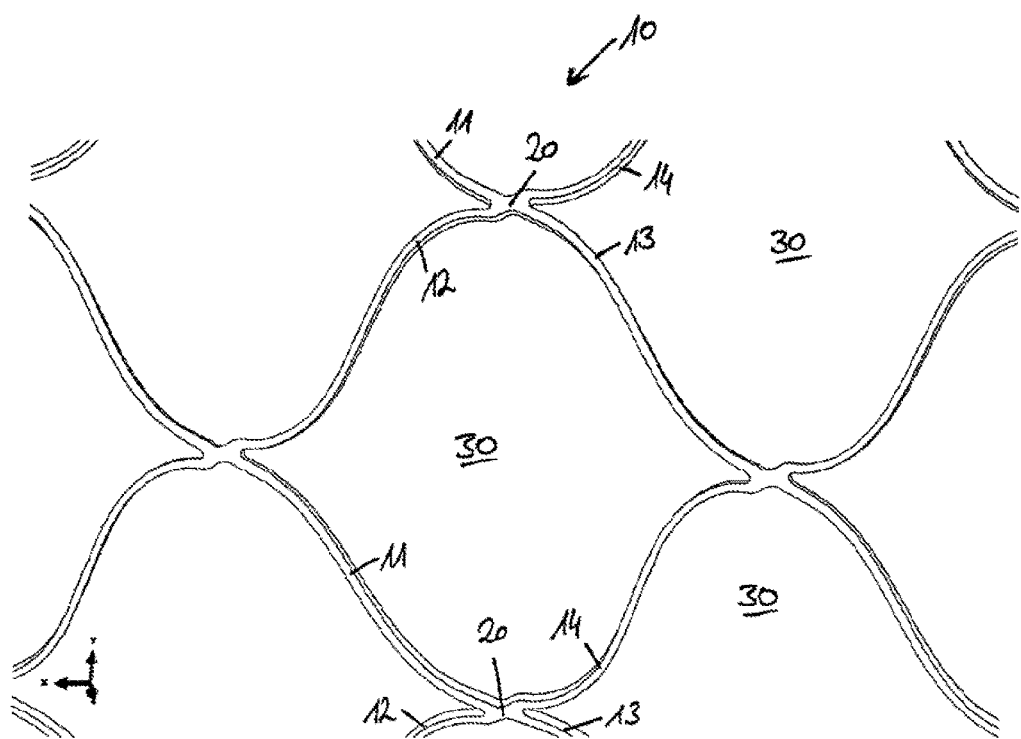
FIG. 9: a lateral view of the medical device according to FIG. 1 in the production state, in particular at an expansion degree of 100%.

The cells 30 have essentially the basic form of a rhomboid. In FIG. 9, this can be clearly seen. In particular, the cells 30 are delimited by four webs 11, 12, 13, 14 each, wherein the webs 11, 12, 13, 14 can at least in part have a curved course, in particular an S-shaped course. Each cell 30 has cell tips 31, 32 which determine the corner points of the rhomboid basic shape. Each cell tip 31, 32 is arranged on web connectors 20, each of which integrally connects four webs 11, 12, 13, 14 with each other. Four webs 11, 12, 13, 14 each extend from each web connector 20, and each web 11, 12, 13, 14 is assigned to two cells 30. Each web 11, 12, 13, 14 delimits the cells 30.

As a rule, the lattice structure 10 can assume several different states that are distinguished by the expansion degree of the lattice structure 10. An expansion degree of 0% corresponds to a theoretical cross-sectional diameter of 0 mm of the lattice structure 10. In practice, such an expansion degree is not achievable. The smallest expansion degree possible in practice is preferably not higher than 10%. In this maximally compressed state the lattice structure 10 is guided to the treatment site through a catheter. Within the framework of the application, this state is called the guiding state. In the embodiments shown in the figures, the lattice structure 10 has an expansion degree of 9.9% in the guiding state.

FIG. 1 shows the lattice structure 10 in the guiding state. It can be clearly seen that the webs 11, 12, 13, 14 partially rest against each other in a circumferential direction, thus blocking any further compression. In other words, the web width of the individual webs 11, 12, 13, 14 restricts the compressibility of the lattice structure 10. It can also be seen that each of the web connectors 20 is essentially arranged on a common circumferential line. Overall, several cells 30 thus form a cell ring 34 in a circumferential direction of the lattice structure 10. The entire lattice structure 10 is formed by several cell rings 34 that are connected with each other longitudinally.

It is pointed out in this connection that the lattice structure 10 can only be formed in some sections from interconnected cell rings that have the same cross-sectional diameter. It is in fact also possible for the lattice structure 10 to have, in some sections, a geometry other than a cylindrical one. The lattice structure can, at least at one proximal end, be funnel-shaped, for example. A configuration of this type is of advantage in medical devices that are used as thrombus catchers or generally as thrombectomy devices. In such cases, the lattice structure 10 can essentially form a basket-like structure. Lattice structures 10 that are entirely cylindrical are used in medical devices that form stents. Stents can be used to support blood vessels, or generally in hollow body organs and/or to cover aneurysms.

In FIG. 2, a web connector 20 of the lattice structure 10 according to FIG. 1 is shown in detail. The web connector 20 interconnects four webs 11, 12, 13, 14. For simplicity's sake, within the framework of the application, the webs 11, 12, 13, 14 that are merged at a web connector 20 are numbered counter-clockwise to allow for a clear allocation. This allows a first web 11 and a second web 12 to be assigned to a first cell 30, and a third web 13 and a fourth web 14 to be assigned to a second cell 30, wherein the cells 30 are immediately adjacent to each other in a longitudinal direction of the lattice structure 10. In other words, the web connector 20 separates two cells 30 of the lattice structure 10 that are longitudinally arranged adjacent to each other. In the area of the web connector 20, each cell 30 forms cell tips 31, 32. A first cell tip 31 is bounded by the first web 11 and the second web 12. A second cell tip 32 is delimited by the third web 13 and the fourth web 14.

Each cell tip 31, 32 forms or encompasses a curvature 33. The curvature 33 results from the transition of the lateral surfaces of the adjoining webs 11, 12, 13, 14 that are circumferentially aligned. Specifically, the first cell tip 31 forms a curvature 33 that results from the transition of the first web 11 to the second web 12 in the area of the web connector 20. Accordingly, the curvature 33 of the second cell tip 32 is created by a curved transition between the third web 13 and the fourth web 14 at the web connector 20. The curvatures 33 preferably take a parabolic shape. Each curvature 33 has a maximum or a vertex, i.e., a point where the curvature radius is smallest. The distance between the vertices of the curvatures 33 on opposite sides of a web connector 20 corresponds to the shortest distance between the cell tips 31, 32. The connecting line, i.e., the distance between the two maxima or the vertices of the curvatures 33 forms the connector axis 21. In other words, the connector axis 21 corresponds to the shortest distance between the two curvatures 33 of the first cell tip 31 and the second cell tip 32.

The connector axis 21 identifies the alignment of the web connector 20 with respect to different degrees of expansion. Generally, the angle between the connector axis 21 and the longitudinal axis 15 of the lattice structure 10 changes when the lattice structure 10 is compressed or expanded. In the guiding state, the connector axis 21 is preferably aligned parallel to the longitudinal axis 15 of the lattice structure 10. It is, however, also possible for the connector axis 21 in the guiding state to be arranged at an angle to the longitudinal axis 15 of the lattice structure 10. The angle is preferably not more than 5 degrees, in particular not more than 4 degrees, in particular not more than 3 degrees, in particular not more than 2o, in particular not more than 1 degree.

In the figures, the longitudinal axis 15 of the lattice structure 10 is shown by a dot-dash line with the description "global stent axis." FIG. 2 shows that the cell tips 31, 32 in the guiding state are essentially arranged longitudinally on opposite sides, particularly without any staggering in a circumferential direction. In this configuration, the lattice structure 10 has an especially high axial stability. This is of advantage when the lattice structure 10 is threaded through a catheter. In particular, the cell tips 31, 32 support each other longitudinally-axially, i.e., parallel to the longitudinal axis 15.

When the lattice structure 10 is released from a catheter or any guiding system in general, the lattice structure 10 automatically expands radially. In so doing, the lattice structure 10 passes through several degrees of expansion until the lattice structure 10 attains the implanted state. In the implanted state the lattice structure 10 preferably applies radial force to the surrounding vascular walls. The implanted state preferably corresponds to an expansion degree of the lattice structure 10 that is smaller than 100% and greater than 10%. The implanted state is also known as "intended use configuration."

Figure 3:
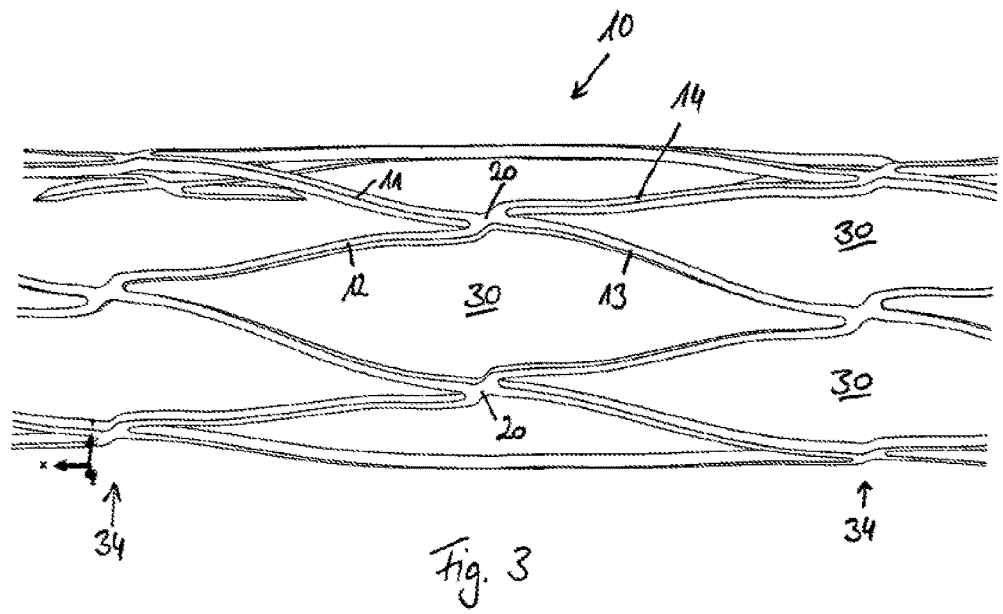
FIG. 3: a lateral view of the medical device according to FIG. 1 in a partially expanded state, in particular at an expansion degree of 44.4%.

In the FIGS. 3-8, the lattice structure 10 or the web connector 20 is shown at different expansion degrees. FIG. 3 thus shows, by way of example, a lateral view of the lattice structure 10 at a degree of expansion of 44.4%. In spite of the radial expansion of the lattice structure 10, it is easy to see that the web connectors 20 are further arranged on a common circumferential line. In particular, upon the expansion of the lattice structure 10 no longitudinal-axial staggering of the various web connectors 20 takes place. The cells 30 noticeably expand, causing the adjacent webs 11, 12, 13, 14 to unfold chevron-like in a circumferential direction. Thus, as the lattice structure 10 expands, the cell height, measured in the circumferential direction of the lattice structure 10, increases. Simultaneously, due to the foreshortening effect the cell width is reduced, determining the width of the cell 30 in the longitudinal direction of the lattice structure 10.

Figure 4:
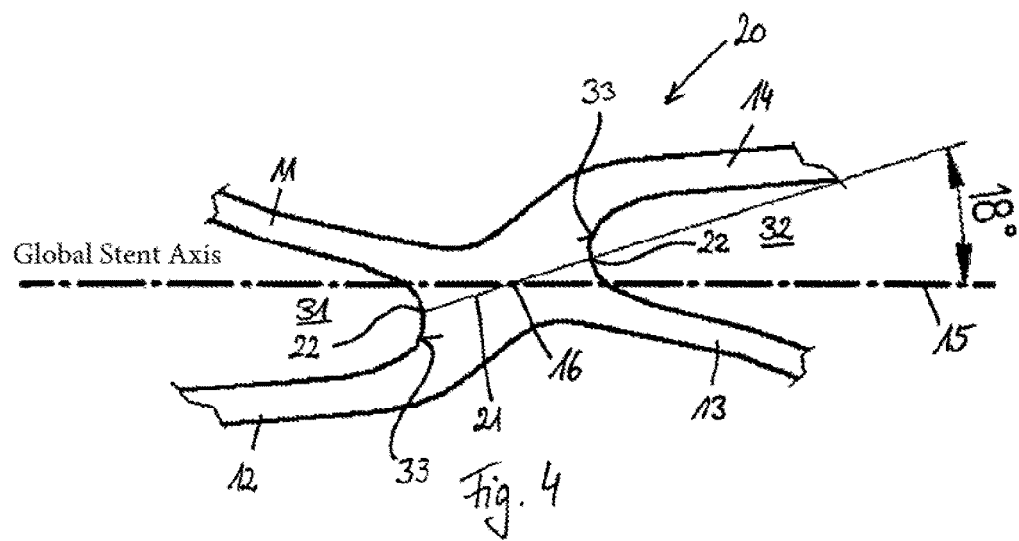
FIG. 4: a detail view of a web connector of the medical device according to FIG. 3.

FIG. 4 shows the web connector 20 of the lattice structure 10 at an expansion degree of the lattice structure 10 of 44.4%. Thus, FIG. 4 is a detail view of FIG. 3. It is easily seen that the cell tips 31, 32 are staggered to each other by the expansion of the lattice structure 10 circumferentially. In particular, the web connector 20 turns or rotates during the expansion of the lattice structure 10, causing an angular displacement between the connector axis 21 and the longitudinal axis 15 of the lattice structure 10. At an expansion degree of 44.4%, the angular displacement is preferably approximately 18 degrees. Specifically, at an expansion degree of 44.4% an angle is created between the connector axis 21 and the longitudinal axis 15 of the lattice structure 10, said angle assuming a value of 18 degrees. The rotation of the web connector 20 occurs during the transition of the lattice structure 10 from the guiding state up to an expansion degree of 44.4%, or generally of less than 50% essentially in a counter-clockwise direction.

In FIG. 4 it can also be seen that the connector axis 21 transects the longitudinal axis 15 of the lattice structure 10. The intersection between the connector axis 21 and the longitudinal axis 15 of the lattice structure 10 is called the rotation point 16. The rotation point 16 describes the point at the web connector 20 around which the web connector 20 rotates. The web connector 20 thus rotates around the rotation point 16 as the lattice structure 10 expands, during which the rotational direction can change.

Figure 5:
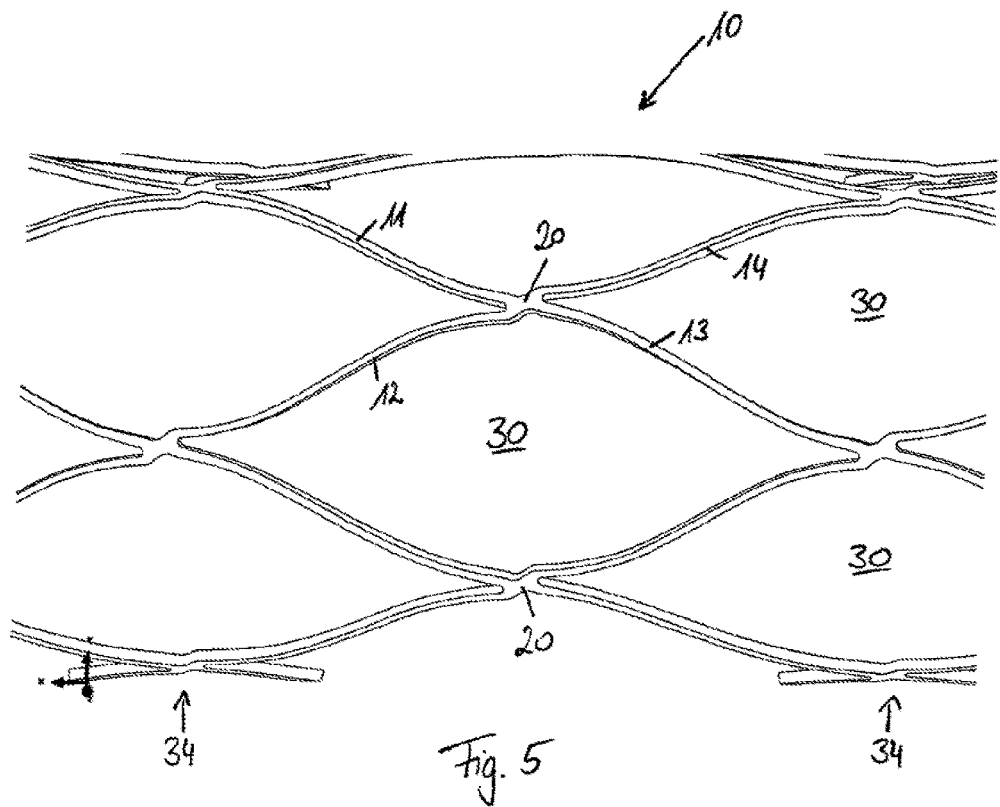
FIG. 5: a lateral view of the medical device according to FIG. 1 in a partially expanded state, in particular at an expansion degree of 66.7%.

FIG. 5 shows a further intermediate state of the lattice structure 10, in particular at an expansion degree of 66.7%. In this state as well, the web connectors 20 continue to be on a common circumferential line. The cells 30, compared to the intermediate state according to FIG. 4, are identifiable by their greater height and a smaller width.

Figure 6:
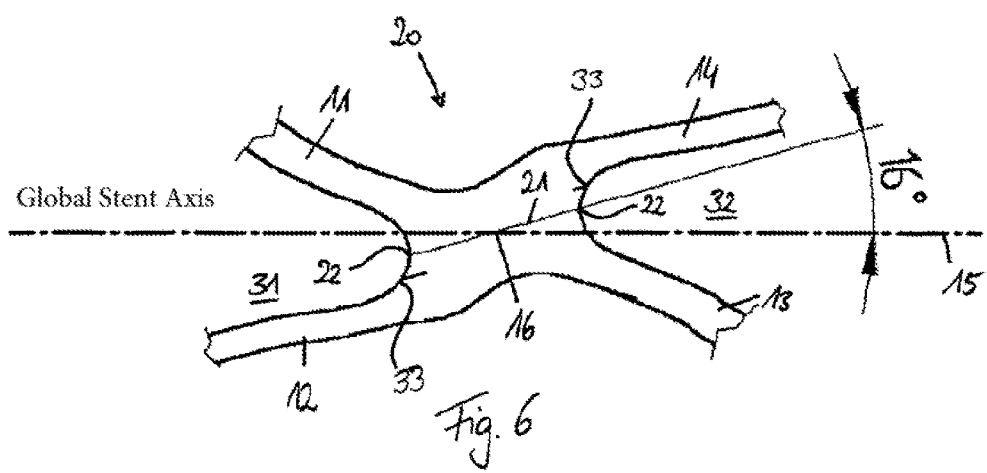
FIG. 6: a detail view of a web connector of the medical device according to FIG. 5.

In the detail view according to FIG. 6, the web connector 20 is shown at an expansion degree of the lattice structure 10 of 66.7%. The web connector 20 has a connector axis 21 that is arranged at an angle of 16 degrees to the longitudinal axis 15 of the lattice structure 10. [The invention] generally provides that, at an expansion degree of greater than 50%, the angle between the connector axis 21 and the longitudinal axis 15 of the lattice structure 10 is smaller than at an expansion degree of the lattice structure 10 of less than 50%. In other words, the rotational direction of the web connector 20 changes when the lattice structure 10 expands. The change of the rotational direction occurs preferably at an expansion degree of approximately 50%, in particular at an expansion degree of between 44% and 45%. During the expansion of the lattice structure 10, the web connector 20 first turns counter-clockwise, and then changes its rotational direction to turn in a clockwise direction.

Figure 7:
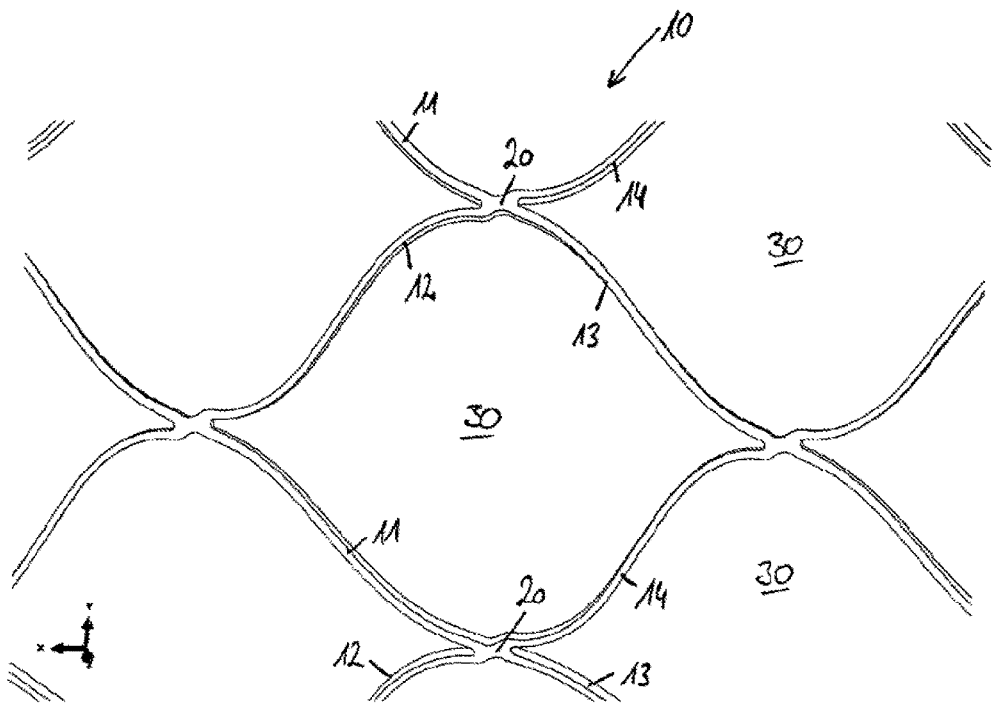
FIG. 7: a lateral view of the medical device according to FIG. 1 in a partially expanded state, in particular at an expansion degree of 88.9%.
Figure 8:
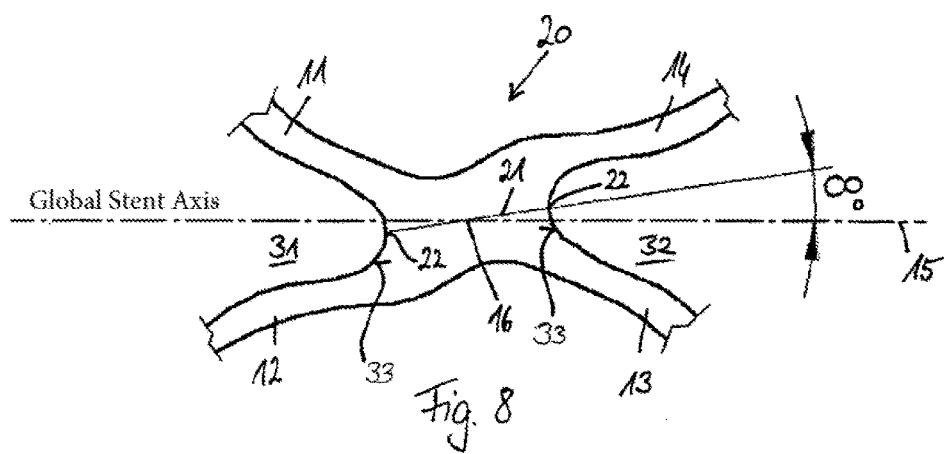
FIG. 8: a detail view of a web connector of the medical device according to FIG. 7.

At an expansion degree of 88.9%, i.e., in an intermediate state as shown in FIGS. 7 and 8, the web connector 20 is at an angle to the longitudinal axis 15 of the lattice structure 10 that is smaller than at an expansion degree of 44.4% and 66.7%. As shown in FIG. 8, the angle displacement between the connector axis 21 and the longitudinal axis 15 of the lattice structure 10 at an expansion degree of 88.9% measures approximately 8 o. In other words, the staggering between the cell tips 31 and 32 changes in a circumferential direction. FIG. 7 shows clearly that during an intermediate state which essentially corresponds to an expansion degree of approximately 90%, the cell height almost approximates the cell width of cell 30. The web connectors 20 of the lattice structure 10 are further arranged on a common circumferential line. The same applies to the web connectors 20 in a longitudinal direction of the lattice structure 10.

In general, when the lattice structure 10 expands, the web connectors 20 of the lattice structure 10 do not change their alignment relative to each other, both circumferentially and longitudinally. Instead, the alignment of the connector axis 21 of each individual web connector 20 is changed. In other words, while the web connectors 20 turn when the lattice structure 10 expands, they essentially maintain their relative position with respect to adjoining web connectors 20 in a longitudinal and circumferential direction. Only the distance between the web connectors 20 is changed, at which the web connectors 20 move away from each other in straight lines of movement or, when the lattice structure 10 is compressed, approach each other.

FIG. 9 shows a lateral view of the lattice structure 10 showing the lattice structure 10 in the production state. In other words, the lattice structure 10 is fully expanded. The lattice structure 10 essentially is in a state free of radial force. In this state the cell 30 has a cell height that essentially corresponds to the cell width. The basic shape of the cell in this case is essentially a square and thus corresponds to an equiangular or a rectangular rhomboid. The webs 11, 12, 13, 14 of cell 30, however, do not extend in a straight line. However, if the cell tips 31 and 32 of the cell are connected to each other in a straight line, a square basic form will essentially be seen.

Figure 10:
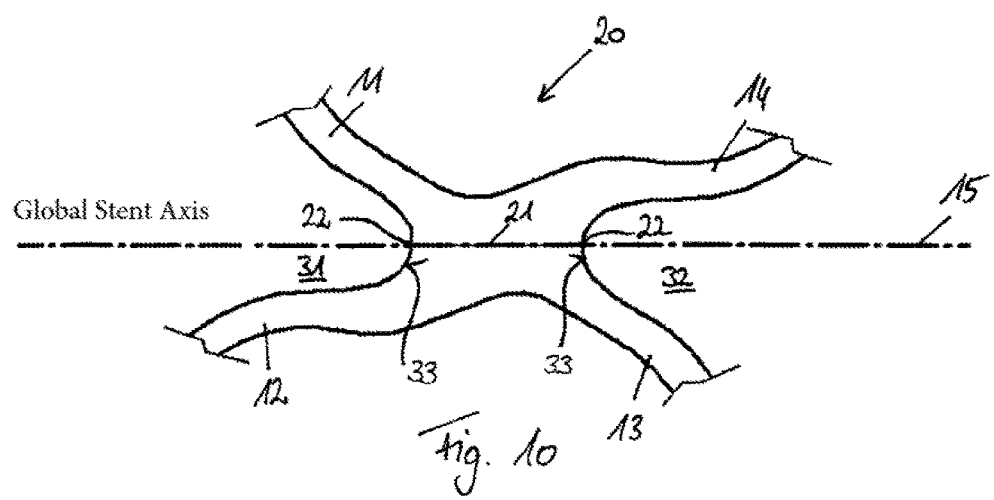
FIG. 10: a detail view of a web connector of the medical device according to FIG. 9.

In FIG. 10 the web connector 20 is shown in detail when the lattice structure 10 is present in the production state according to FIG. 9. As a result of the alternating rotation of the web connector 20 as the lattice structure 10 expands, the web connector 20 in the production state again assumes its original alignment. In particular, the connector axis 21 in the production state is aligned parallel to the longitudinal axis 15 of the lattice structure 10. The cell tips 31, 32 are thus arranged longitudinally along the lattice structure 10 on the web connector 20 on opposite sides. In other words, the cell tips 31, 32 are aligned with each other. It is, however, also possible for the connector axis 21 in the production state to be arranged at an angle to the longitudinal axis 15 of the lattice structure 10. The angle is preferably not more than 5 degree, in particular not more than 4 degrees, in particular not more than 3 degree, in particular not more than 2 degrees, in particular not more than 1 degree.

Figure 11:
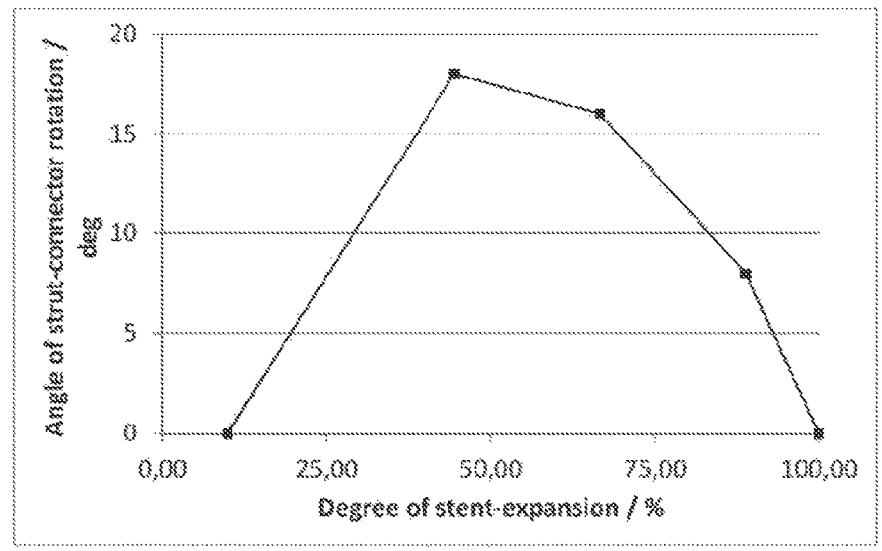
FIG. 11: a diagram showing the angles between the web connector and the longitudinal axis of the lattice structure in relation to the expansion degree in the medical device according to FIG. 1.

FIG. 11 is a diagram of the course of the web connector rotation as the lattice structure 10 expands. Beginning at a guiding state that corresponds to an expansion degree of approximately 10%, the angle between the connector axis 21 and the longitudinal axis 15 of the lattice structure 10 initially increases. In particular, the rotational angle increases to a value of up to approximately 18 degree. This value is reached at an expansion degree of approximately 44% to 45%. The rotational direction of the web connector 20 then changes, decreasing the angle between the connector axis 21 and the longitudinal axis 15 of the lattice structure 10. In particular, the angle between the connector axis 21 and the longitudinal axis 15 of the lattice structure 10 diminishes until the fully expanded state or the production state of the lattice structure 10 is reached. In the production state, i.e., at an expansion degree of 100%, the angle between the connector axis 21 and the longitudinal axis 15 of the lattice structure 10 is 0%. Thus, the connector axis 21 is arranged parallel to the longitudinal axis 15 of the lattice structure 10. In general, the connector axis 21 of the web connector 20 is aligned parallel to the longitudinal axis 15 of the lattice structure 10 when the lattice structure 10 is in the guiding state as well as in the production state. In the intermediate states between the guiding state and the production state, an angle appears between the connector axis 21 and the longitudinal axis 15 of the lattice structure 10.

Figure 12:
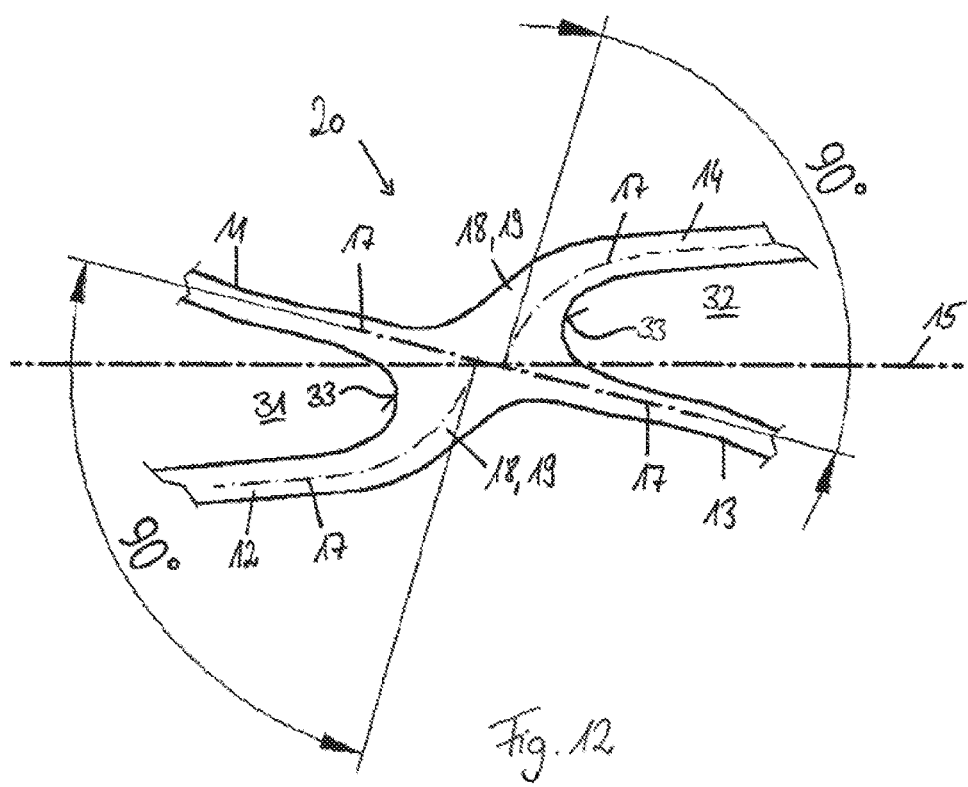
FIG. 12: a detail view of a web connector of the medical device according to FIG. 1 at an expansion degree of 44.4% showing the neutral fibers of the webs.

FIG. 12 shows an exemplary web connector 20 of the lattice structure 10 where the lattice structure 10 is at a degree of expansion of 44.4%. FIG. 12 additionally shows the neutral fibers 17 of the individual webs 11, 12, 13, 14, drawn in a dot-dash line. A further dot-dash line that runs horizontally within the image plane represents the position of the longitudinal axis 15 of the lattice structure 10.

A total of four webs 11, 12, 13, 14 converge at the web connector 20. The webs 11, 12, 13, 14 are distinguished, on the one hand, by their shape and, on the other hand, by their web width. In particular, a first web 11 and a third web 13 have a web width that is smaller than the web width of the second web 12 and the fourth web 14. This considers the average web width. It can also be seen that the first web 11 and the third web 13, essentially aligned with each other in a straight line, debouch into the web connector 20. Specifically, the first web 11 and the third web 13 each have a neutral fiber 17, wherein the neutral fibers 17 of the first web 11 and the third web 13 are aligned with each other. Thus, the neutral fibers 17 of the first web [11] and the third web 13 essentially merge into each other in a straight line, so that a common neutral fiber 17 is created that traverses the web connector 20.

The second web 12 and the fourth web 14 differ in shape from the first web 11 and the third web 13. Characteristic for the second web 12 and the fourth web 14 is their curved course in the area of the web connector 20. Specifically, the second web 12 and the fourth web 14 each have an angular end section 19. The angular end sections 19 each form a root 18 of the second web 12 and the fourth web 14. Specifically, the second web 12 and the fourth web 14 each have a broadened root 18.

Figure 14:
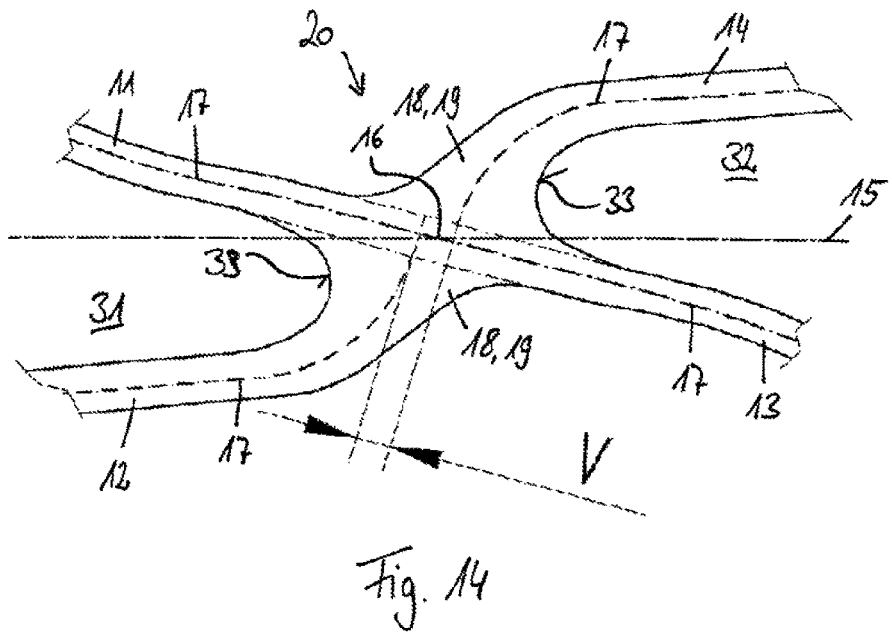
FIG. 14: a detail view of the web connector according to FIG. 12, showing the staggering of the neutral fibers of diametrically opposite webs.

The diametrically opposing webs 12, 14, described as the second web 12 and the fourth web 14, essentially debouch staggered to each other into the web connector 20. The course of the neutral fibers 17 of webs 11, 12, 13, 14 shows this clearly. Both the second web 12 and the fourth web 14 each have a neutral fiber 17 that meets the neutral fiber, in particular the common neutral fiber 17, of the first web 11 and the third web 13 at an angle. The angle between the neutral fiber 17 of the second web 12 and the common neutral fiber 17 of the first web [11] and the third web 13 preferably measures 90 degrees. The same applies to the neutral fiber 17 of the fourth web 14 which also meets the common neutral fiber 17 of the first web 11 and the third web 13 at a preferred angle of 90 degrees. The neutral fibers 17 of the second web 12 and the fourth web 14, by contrast, are aligned to each other in staggered fashion. FIG. 14 shows the web connector 20 of FIG. 12 illustrating the fiber displacement V between the neutral fibers 17 of the second web 12 and the fourth web 14.

On principle, an angle of 90 degrees between the neutral fibers of the second web and the fourth web with respect to the common neutral fiber 17 of the first web 11 and the third web 13, i.e., a vertical alignment is preferred. However, different angles are also possible. The neutral fibers of the second web 12 and the fourth web 14, for example, can also meet the common neutral fiber 17 of the first web 11 and the third web 13 at an angle of less than 90 degrees, in particular not more than 75 degrees, in particular not more than 55 degrees, in particular not more than 50 degrees, in particular not more than 45 degrees.

In general, FIG. 12 shows that the first web 11 and the third web 13 are essentially arranged in line with each other or true to the line. By contrast, the second web 12 and the fourth web 14 take an S-shaped course in the area of the web connector 20. The angular end sections 19 of the second web 12 and the fourth web 14 form an intermediate section, formed by the web connector 20, between two opposing bends of the S-shaped course of the two diametrically opposite webs 12, 14, that are described as the second web 12 and the fourth web 14.

Figure 13:
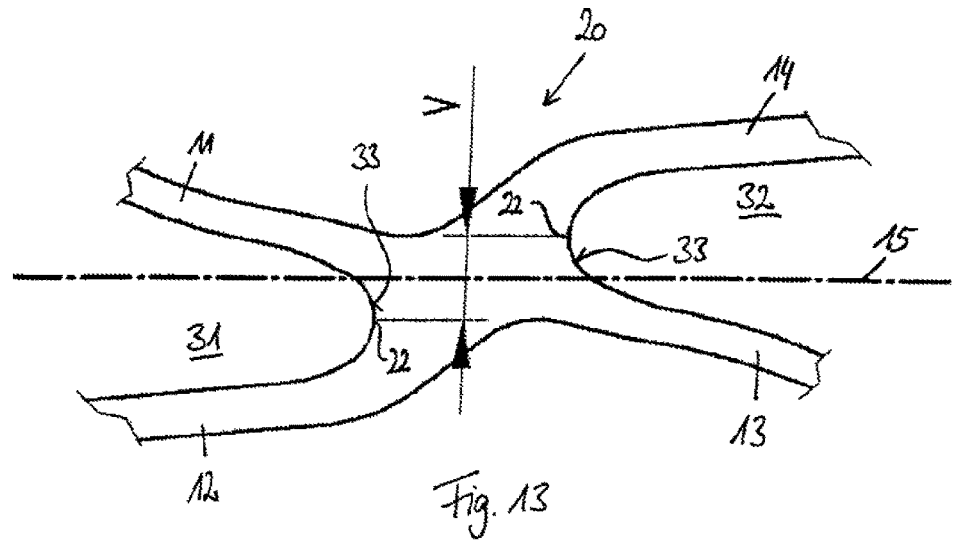
FIG. 13: a detail view of the web connector according to FIG. 12, showing the longitudinal displacement of the cell tips of neighboring cells.

FIG. 13 shows, by way of clarification, the web connector according to FIG. 12, which clearly shows the displacement between the cell tips 31, 32 in a circumferential direction. The web connector 20 according to FIG. 13 has a connector axis 21 that is arranged in an angular displacement to the longitudinal axis 15 of the lattice structure 10. The angular displacement is preferably approximately 18 degrees. In other words, FIG. 13 shows the web connector 20 at an expansion degree of the lattice structure 10 of approximately 44.4%. In this intermediate state of the lattice structure 10, there exists a circumferential displacement V between the end points 22 of the connector axis 21, said displacement being shown by appropriate arrows in FIG. 13. The circumferential displacement V in relation to the web width of the second web 12 and the fourth web 14 is preferably at least 0.5, in particular at least 1.0, in particular at least 1.5, in particular at least 2.0. In the embodiment according to FIG. 13, the circumferential displacement V in relation to the web width of the second web 12 and the fourth web 14 is 1.0. In other words, the circumferential displacement of the cell tips 31, 32 or of the end points 22 of the connector axis 21 corresponds to the web width of the second web 12 or the fourth web 14. The circumferential displacement V is a function of the angular displacement. In this respect, the circumferential displacement V in the guiding state and/or the production state of the lattice structure 10 is preferably zero.

On principle, the invention provides that the rotation of the web connector 20 can be not more than 30 degrees, in particular not more than 20 o, in particular not more than 18 degrees, in particular not more than 15 degrees, in particular not more than 10 degrees, in particular not more than 5 degrees. In the embodiments illustrated the angular displacement between the connector axis 21 and the longitudinal axis 15 of the lattice structure 10 is a maximum of 18 degrees, in particular at an expansion degree of the lattice structure 10 of 44.4%.

For increased flexibility, it is of advantage for the webs 11, 12, 13, 14 to have different web width. Diametrically opposite webs, particularly the first web 11 and the third web 13, can have a first web width and crosswise arranged, diametrically opposite webs; particularly the second web 12 and the fourth web 14 can have a second web width. The ratio between the first web width and the second web width, i.e., the web width ratio, can be at least 1:1.25, in particular at least 1:1.5, in particular at least 1:1.75, in particular at least 1:2.

A web width ratio of 1:1.2 or 1:1.3 was found to be particularly suitable, in particular for a lattice structure 10 that has six cells 30 in the circumferential direction. For a lattice structure 10 having more than twelve cells 30 that are arranged immediately adjacent to each other circumferentially, the web width ratio is preferably 1:1.2 or 1:1.25, respectively.

In principle, the flexibility of the lattice structure 10 is increased when a relatively small web width ratio is chosen. At a web width ratio of 1:1.25 (the web width of the first web 11 or the third web 13, respectively, to the web width of the second web 12 or the fourth web 14, respectively), an especially high flexibility has been observed, since this leads to an improved rotation of the web connector 20. At the same time, a web width ratio of this type provides a sufficient expansion force.

In general, [the invention] also provides for the lattice structure 10 to have a maximum of 48, in particular a maximum of 24, in particular a maximum of 16, in particular a maximum of 12, in particular a maximum of 6 cells 30 in a circumferential direction. In other words, each cell ring 34 of the lattice structure 10 can be formed of a maximum of 48, in particular a maximum of 24, in particular a maximum of 16, in particular a maximum of 12, in particular a maximum of 6 cells.

In a specific embodiment, the medical device forms a stent having a lattice structure 10. The lattice structure 10 or the stent can have an outer diameter in the production state of 3.5 mm or 4.5 mm respectively. The axial length of the stent or the lattice structure 10, is preferably 15 mm, 20 mm or 35 mm. The web width ratio is preferably 1:1.25, wherein the first web width is 40 μm and the second web width is 32 μm. The lattice structure 10 preferably takes the form of a six-cell lattice structure 10, i.e., the lattice structure 10 has cell rings 34 with six cells 30 each.

In principle, the invention is suited not only for use as a stent, but also as a clot retriever or flow diverter, particularly when the lattice structure 10 is laser-cut.

LIST OF REFERENCE SYMBOLS

10 Lattice structure
11 first web
12 second web
13 third web
14 fourth web
15 Longitudinal axis
16 Rotation point
17 Neutral fiber
18 Root
19 Angular end section
20 Web connector
21 Connector axis
22 End point
30 Cell
31 First cell tip
32 Second cell tip
33 Curvature
34 Cell ring

What is claimed is:
1. A medical device for inserting into a hollow organ of the body, the medical device comprising:
   a lattice structure comprises an expanded state, a compressed state, and an intermediate state, the intermediate state being between the expanded state and the compressed state;
   the lattice structure having a longitudinal axis defining a longitudinal direction;
   the lattice structure comprising a plurality of webs and a plurality of closed cells, each web of the plurality of webs bounding one cell of the plurality of closed cells; and
   a plurality of web connectors, each web connector integrally connecting a first web of the plurality of webs to a second web of the plurality of webs, each web connector having a connector axis extending between a first cell and a second cell of the plurality of cells, the first cell and the second cell are adjacent in the longitudinal direction;
   wherein when the lattice structure is in the expanded state, the connector axis and the longitudinal axis are offset from each other by a first angle;

wherein when the lattice structure is in the intermediate state, the connector axis and the longitudinal axis are offset from each other by a second angle; the second angle being larger than the first angle; and wherein each cell of the plurality of closed cells comprises a cell tip, the connector axis being along a shortest distance between a first cell tip of the first cell and a second cell tip of the second cell.

2. The medical device of claim 1, wherein the first angle is 5 degrees or less.

3. The medical device of claim 1, wherein the first angle is substantially 0 degrees.

4. The medical device of claim 1, wherein when the lattice structure is in the expanded state, at least one web connector of the plurality of web connectors has a first rotational direction;

when the lattice structure is in the compressed state, the at least one web connector has a second rotational direction, the second rotational direction being different than the first rotational direction.

5. The medical device of claim 1, wherein each of the first cell tip and the second cell tip comprise a curvature having a vertex, the vertex forming an end point of the connector axis.

6. The medical device of claim 1, further comprising a rotation point around which a respective web connector rotates, wherein when the lattice structure is in intermediate state, the rotation point is disposed at an intersection of the longitudinal axis and a transection of the longitudinal axis by the connector axis.

7. The medical device of claim 6, wherein the web connector is formed point-symmetrically relative to the rotation point.

8. The medical device of claim 1, wherein the plurality of webs further comprises a third web and a fourth web, wherein the first, second, third, and fourth web are disposed adjacent to the respective web connector;

wherein the first web and the third web are arranged on a diametrically opposite side to the second web and the fourth web.

9. The medical device of claim 8, further comprising a plurality of neutral fibers, a first neutral fiber being associated with the first web and the third web, a second neutral fiber being associated with the second web and the fourth web, the first neutral fiber being positioned on the second neutral fiber.

10. The medical device of claim 8, further comprising a plurality of neutral fibers, a first set of neutral fibers being associated with the first web and the third web, a second set of neutral fibers being associated with the second web and the fourth web;

wherein the first set of neutral fibers is arranged so that the neutral fibers of the first set of neutral fibers are in a staggered fashion to each other; and wherein the second set of neutral fibers is arranged so that the neutral fibers of the second set of neutral fibers are aligned with each other.

11. The medical device of claim 10, wherein each of the first web and the second web comprises a broadened root.

12. The medical device of claim 8, wherein the first web and the second web are S-shaped proximal to the respective web connector or the second web and the fourth web have a straight shape proximal to the respective web connector.

13. The medical device of claim 1, wherein at least one web connector has a wasp-waisted shape.

14. The medical device of claim 1, wherein the connector axis is offset to the longitudinal axis by 5 degrees or less when the lattice structure has an expansion degree of 15% or less or 90% or more.

15. The medical device of claim 1, wherein the connector axis is offset from the longitudinal axis by 15 degrees to 20 degrees when the lattice structure has an expansion degree of 40% to 50%.

16. The medical device of claim 1, wherein the connector axis is offset from the longitudinal axis by 12 degrees to 18 degrees when the lattice structure has an expansion degree of 60% to 70%.

17. The medical device of claim 1, wherein the connector axis is offset from the longitudinal axis by 5 degrees to 12 degrees when the lattice structure has an expansion degree of 80% to 90%.

18. The medical device of claim 1, wherein the lattice structure is self-expandable.

19. The medical device of claim 1, wherein the lattice structure comprises nitinol.

20. The medical device of claim 1, where when the lattice structure is in the expanded state, the lattice structure has a cross-sectional diameter between 3.5 mm and 6 mm.

21. The medical device of claim 1, wherein the lattice structure has, in the circumferential direction, between three and six immediately adjacent cells that form a cell ring and are bounded by four webs each, of which the first web and a third web has a first web width, and the second web and a fourth web each has a second web width, wherein a ratio between the first web width and the second web width is between 1:1.1 and 1:1.5.

22. The medical device of claim 1, wherein the lattice structure has, in the circumferential direction, more than 12 immediately adjacent cells that form a cell ring and are bounded by four webs each, of which the first web and a third web each has a first web width, and the second web and a fourth web each has a second web width, wherein a ratio between the first web width and the second web width is between 1:1.1 and 1:3.

* * * * *